(12) United States Patent
Ruano Plaza

(10) Patent No.: US 12,319,658 B2
(45) Date of Patent: Jun. 3, 2025

(54) PYRIMIDINE-5-CARBOXAMIDE COMPOUND

(71) Applicant: Eli Lilly and Company, Indianapolis, IN (US)

(72) Inventor: Sra. Gema Ruano Plaza, Alcobendas (ES)

(73) Assignee: Eli Lilly and Company, Indianapolis, IN (US)

( * ) Notice: Subject to any disclaimer, the term of this patent is extended or adjusted under 35 U.S.C. 154(b) by 796 days.

(21) Appl. No.: 17/631,672

(22) PCT Filed: Jul. 31, 2020

(86) PCT No.: PCT/US2020/044394
§ 371 (c)(1),
(2) Date: Jan. 31, 2022

(87) PCT Pub. No.: WO2021/025975
PCT Pub. Date: Feb. 11, 2021

(65) Prior Publication Data
US 2022/0274933 A1    Sep. 1, 2022

(30) Foreign Application Priority Data

Aug. 6, 2019  (EP) .................................. 19382686
Sep. 9, 2019  (EP) .................................. 19382744

(51) Int. Cl.
C07D 239/48    (2006.01)
A61P 3/10      (2006.01)
A61P 13/12     (2006.01)

(52) U.S. Cl.
CPC .............. *C07D 239/48* (2013.01); *A61P 3/10* (2018.01); *A61P 13/12* (2018.01)

(58) Field of Classification Search
CPC ........... C07D 239/48; A61P 3/10; A61P 13/12
See application file for complete search history.

(56) References Cited

FOREIGN PATENT DOCUMENTS

WO      2012/145569      10/2012
WO      WO-2012145569 A1 * 10/2012 ........... A61K 31/505

OTHER PUBLICATIONS

International Search Report of the International Searching Authority pertaining to International Application No. PCT/US2020/044394; Date of Mailing: Sep. 21, 2020; 6 pages.
Written Opinion of the International Searching Authority pertaining to International Application No. PCT/US2020/044394; Date of Mailing: Sep. 21, 2020; 8 pages.
Ruf, S., Hallur, M. S., Anchan, N. K., Swamy, I. N., Murugesan, K. R., Sarkar, S., . . . & Rajagopal, S. (2018). Novel nicotinamide analog as inhibitor of nicotinamide N-methyltransferase. *Bioorganic & medicinal chemistry letters*, 28(5), 922-925.
Lee, H. Y., Suciu, R. M., Horning, B. D., Vinogradova, E. V., Ulanovskaya, O. A., & Cravatt, B. F. (2018). Covalent inhibitors of nicotinamide N-methyltransferase (NNMT) provide evidence for target engagement challenges in situ. Bioorganic & medicinal chemistry letters, 28(16), 2682-2687.

* cited by examiner

*Primary Examiner* — James H Alstrum-Acevedo
*Assistant Examiner* — Justin Christopher Sanchez
(74) *Attorney, Agent, or Firm* — MaCharri Vorndran-Jones

(57) ABSTRACT

The present invention provides a compound of the formula: or a pharmaceutically acceptable salt thereof, and methods of using this compound for treating type 2 diabetes mellitus.

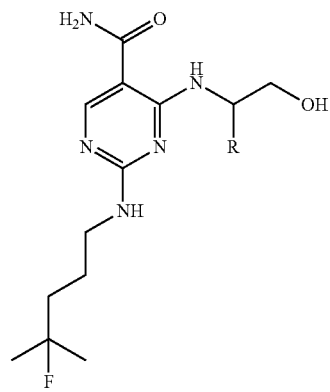

7 Claims, No Drawings

PYRIMIDINE-5-CARBOXAMIDE COMPOUND

This invention relates to a pyrimidine-5-carboxamide compound, pharmaceutically acceptable salts thereof, a pharmaceutical composition, and therapeutic uses of the compound.

Nicotinamide N-methyltransferase (NNMT) is an enzyme that catalyzes the transfer of a methyl group from the universal methyl donor S-(5'-Adenosyl)-L-methionine (SAM) onto nicotinamide (NAM) resulting in the formation of 1-methyl nicotinamide (1-MeNAM). NNMT is a potential therapeutic target for treatment of type 2 diabetes mellitus (T2DM).

WO 2018/183668 discloses certain quinoline derivatives, which are described as NNMT inhibitors. Bisubstrate small molecule inhibitors of NNMT have also been described (Martin, N. I.; et al., "Bisubstrate Inhibitors of Nicotinamide N-Methyltransferase (NNMT) with Enhanced Activity", *Journal of Medicinal Chemistry*, 2019, 62, 6597-6614). Analogs of nicotinamide have also been reported as NNMT inhibitors (see Rajagopal, S.; Ruf, S.; et al. "Novel nicotinamide analog as inhibitor of nicotinamide N-methyltransferase", *Bioorganic and Medicinal Chemistry Letters*, 2018, 28, 922-925, and Dhakshinamoorthy, S.; Kannt, A.; et al. "A small molecule inhibitor of Nicotinamide N-methyltransferase for the treatment of metabolic disorders", *Scientific Reports*, 2018, 8, 3660.). To date no NNMT inhibitors have been approved for therapeutic use.

Alternative NNMT inhibitor compounds and treatment methods using the same are desired. In particular, NNMT inhibitor compounds which are efficacious and orally bioavailable are desired.

To that end, in an embodiment, the present invention provides a novel compound, which is a potent NNMT inhibitor for treating T2DM.

In an embodiment, the present invention provides a compound of Formula I,

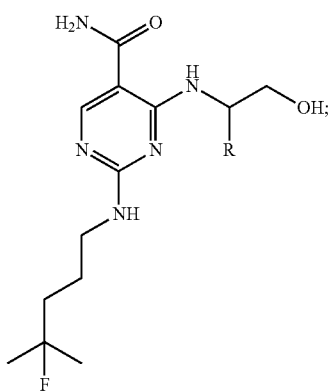

Wherein
R is selected from the group consisting of cyclopropyl and geminal cyclopropyl;
or a pharmaceutically acceptable salt thereof. Formula I includes all individual enantiomers and diastereomers thereof, as well as mixtures of enantiomers and racemates.

In an embodiment, the present invention provides a compound of Formula Ia,

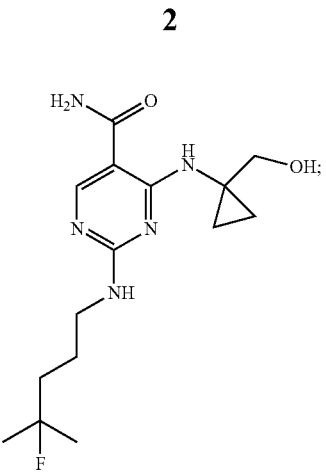

or a pharmaceutically acceptable salt thereof.

In an embodiment, the present invention provides a compound of Formula Ib,

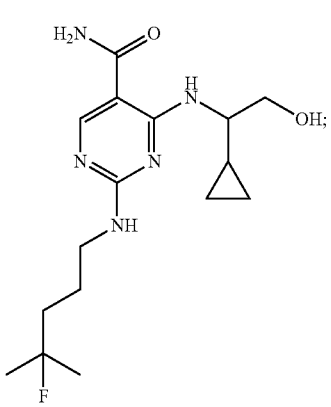

or a pharmaceutically acceptable salt thereof. Formula Ib includes all individual enantiomers thereof, as well as mixtures of enantiomers and racemates.

In another embodiment, the present invention provides a pharmaceutical composition comprising a compound according to Formula I, or a pharmaceutically acceptable salt thereof, and at least one of a pharmaceutically acceptable carrier, diluent, or excipient. In a preferred embodiment, the pharmaceutically acceptable composition is formulated for oral administration.

In another embodiment, the present invention provides a method of treating a mammal for T2DM, the method comprises administering to the mammal in need of treatment a pharmaceutically acceptable composition comprising an effective amount of a compound of Formula I, or a pharmaceutically acceptable salt thereof, and at least one of a pharmaceutically acceptable carrier, diluent or excipient. In one embodiment, the pharmaceutically acceptable composition is formulated for oral administration. Preferably the mammal is a human.

In another embodiment, the present invention also provides a method for treating a mammal for T2DM, the method comprises administering to the mammal in need of treatment an effective amount of a compound according to Formula I, or a pharmaceutically acceptable salt thereof.

In another embodiment, the present invention provides a method of treating metabolic syndrome in a mammal, the method comprises administering to the mammal in need of treatment an effective amount of a compound according to Formula I, or a pharmaceutically acceptable salt thereof.

In another embodiment, the present invention also provides a method of treating chronic kidney disease (CKD) in a mammal, the method comprises administering to the mammal in need of treatment an effective amount of a compound according to Formula I, or a pharmaceutically acceptable salt thereof.

In an embodiment, the present invention provides a compound according to Formula I, or a pharmaceutically acceptable salt thereof, for use in therapy.

In another embodiment, the present invention also provides a compound according to Formula I, or a pharmaceutically acceptable salt thereof, for use in the treatment of T2DM in a mammal.

In another embodiment, the present invention also provides a compound according to Formula I, or a pharmaceutically acceptable salt thereof, for use in the treatment of metabolic syndrome in a mammal.

In another embodiment, the present invention also provides a compound according to Formula I, or a pharmaceutically acceptable salt thereof, for use in treating CKD in a mammal.

In an embodiment, the present invention provides the use of a compound according to Formula I, or a pharmaceutically acceptable salt thereof, for the manufacture of a medicament for the treatment of T2DM in a mammal.

In an embodiment, the present invention provides the use of a compound according to Formula I, or a pharmaceutically acceptable salt thereof, for the manufacture of a medicament for treating metabolic syndrome in a mammal.

In an embodiment, the present invention also provides for the use of a compound according to Formula I or a pharmaceutically acceptable salt thereof in the manufacture of a medicament to treat CKD in a mammal.

In a preferred embodiment, the compound according to Formula I is administered orally. In another preferred embodiment, the mammal to be treated is a human.

As used herein, the term "geminal" has the ordinary meaning recognized by a skilled chemist. That is, the carbons of the cyclopropyl are directly attached to the carbon at the point of substitution, forming an attached cyclopropyl group.

As used herein, the terms "treating", "to treat", or "treatment", refers to lowering, reducing, or reversing the progression or severity of an existing symptom, disorder, or condition. Such conditions could include T2DM and metabolic syndrome.

As used herein, the term "patient" refers to a mammal. Preferably, the patient is human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of the present invention is formulated as a pharmaceutical composition administered by any route which makes the compound bioavailable. Preferably, such a composition is for oral administration. Such pharmaceutical compositions and processes for preparing same are well known in the art (See, e.g., Remington, J. P., "Remington: The Science and Practice of Pharmacy", L. V. Allen, Editor, 22nd Edition, Pharmaceutical Press, 2012).

A compound of Formula I is readily converted to and may be isolated as a pharmaceutically acceptable salt. Salt formation can occur upon the addition of a pharmaceutically acceptable acid to form the acid addition salt or by the addition of a pharmaceutically acceptable base to form a base addition salt. Salts can also form simultaneously upon deprotection of a nitrogen or oxygen, i.e., removing the protecting group. Examples, reactions and conditions for salt formation can be found in Gould, P. L., "Salt selection for basic drugs," International Journal of Pharmaceutics, 33: 201-217 (1986); Bastin, R. J., et al. "Salt Selection and Optimization Procedures for Pharmaceutical New Chemical Entities," Organic Process Research and Development, 4: 427-435 (2000); and Berge, S. M., et al., "Pharmaceutical Salts," Journal of Pharmaceutical Sciences, 66: 1-19, (1977).

Increased expression and activity of NNMT has been linked to various disease pathologies including metabolic syndrome, cardiovascular disease, neurodegeneration, and cancer. Of particular interest is the correlation exhibited between adipose NNMT activity and insulin resistance. This mechanism appears to be reversible, as adipose NNMT activity was reduced following interventions that improve insulin resistance (i.e. bariatric surgery and lifestyle interventions, see Kannt, A.; Pfenninger, A.; Teichert, L; et al. "Association of nicotinamide-N-methyltransferase mRNA expression in human adipose tissue and the plasma concentration of its product, 1-methylnicotinamide, with insulin resistance". *Diabetologia*, 2015, 58, 799-808). Genetic knock down of the NNMT gene in mice showed protective effects against diet-induced obesity and the animals displayed enhanced insulin sensitization, validating its potential utility as a therapeutic target for metabolic disorder and type 2 diabetes mellitus (Kraus D, Yang Q, Kong D, et al. "Nicotinamide N-methyltransferase knockdown protects against diet-induced obesity". *Nature*, 2014, 508, 258-262).

An additional utility for an NNMT inhibitor, as a therapeutic target of interest in metabolic disorders, is its role in regulating methylation capacity of the cell via SAM utilization. The methylation of NAM via NNMT utilizes a methyl group from the universal methyl donor SAM, which converts SAM into its demethylated form S-Adenosyl-L-homocysteine (SAH). SAH is a substrate for the enzyme Adenosylhomocysteinase to convert SAH into homocysteine. Elevated levels of homocysteine (hyperhomocysteinemia) are observed in chronic and end stage kidney disease patients, and is believed to contribute to imbalances of cellular homeostasis and redox resulting in increased oxidative stress (Ostrakhovitch, E. A.; Tabibzadeh S. "Homocysteine in Chronic Kidney Disease", *Advances in Clinical Chemistry*, 2015, 72, 77-106). Amelioration of hyperhomocysteinemia in these patients, via NNMT inhibition, may serve as a valuable therapeutic mechanism for the treatment of chronic kidney disease.

The compound of the present invention, or salts thereof, may be prepared by a variety of procedures, some of which are illustrated in the Preparation and Example below. The products of each step in the Preparation and Example below can be recovered by conventional methods, including extraction, evaporation, precipitation, chromatography, filtration, trituration, and crystallization. Individual isomers, enantiomers, and diastereomers may be separated or resolved at any convenient point in the synthesis, by methods such as, selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "Stereochemistry of Organic Compounds", Wiley-Interscience, 1994).

Certain abbreviations are defined as follows: "EtOAc" refers to ethyl acetate; "HPLC" refers to high-performance liquid chromatography; "NMP" refers to N-methyl-2-pyrrolidinone; "RT" refers to room temperature; and "SFC" refers to supercritical fluid chromatography.

Preparation 1

2-Chloro-4-[[1-(hydroxymethyl)cyclopropyl]amino]pyrimidine-5-carboxamide

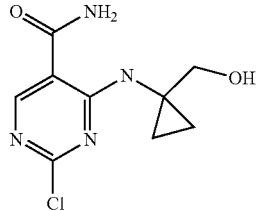 [SMILES: NC(=O)c1cnc(Cl)nc1NC1(CO)CC1]

To a solution of 2,4-dichloropyrimidine-5-carboxamide (10 g, 52 mmol) in NMP (50 mL) at RT add N,N-diisopropylethylamine (27 mL, 155 mmol) and then (1-aminocyclopropyl)methanol hydrochloride (6.95 g, 56.2 mmol) portionwise, observing a slight exotherm during the addition (up to 32° C. within 10 min). Stir the suspension at RT under nitrogen. After 1 h 15 min pour the reaction mixture into a mixture of water and ice (500 mL) and stir for one hour. Filter the solid and wash with water 3 times, then dry in a vacuum oven at 45° C. overnight to give the title compound (11.05 g, 85%) as a beige solid. ES/MS m/z 243 (M+H).

EXAMPLE 1

2-[(4-Fluoro-4-methyl-pentyl)amino]-4-[[1-(hydroxymethyl)cyclopropyl]amino]pyrimidine-5-carboxamide

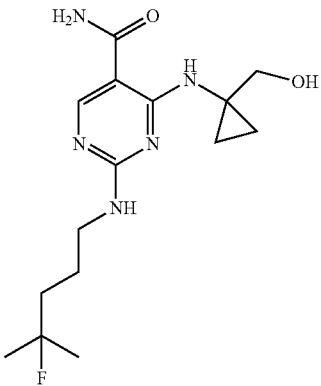 [SMILES: CC(C)(F)CCCNc1ncc(C(N)=O)c(NC2(CO)CC2)n1]

To a solution of 2-chloro-4-[[1-(hydroxymethyl)cyclopropyl]amino]pyrimidine-5-carboxamide (88.3 g, 346 mmol) in NMP (450 mL) at RT add potassium carbonate (143 g, 1034 mmol) and then 4-fluoro-4-methyl-pentan-1-amine acetic acid salt (68.5 g, 382 mmol). Heat the mixture at 80° C. under nitrogen. After 2 hours, cool the reaction mixture to RT and pour over a mixture of ice/water (2000 mL). Stir the mixture overnight. Filter off the solid, wash with water, and dry in a vacuum oven overnight at 45° C. to obtain a beige solid. Mix the solid with ethanol (850 mL) and heptane (850 mL), heat until a solution is obtained using a 95° C. bath, and then let the mixture slowly cool down to RT overnight. Cool the mixture in an ice-water bath for 30 minutes, filter the solid, and wash with heptane. Dry the solid in a vacuum oven. In order to remove residual ethanol, add EtOAc (850 mL) and heat the mixture in a 75° C. bath for 2 h. Let the mixture slowly cool to RT overnight. Concentrate in-vacuo to reduce the mixture to about one third of its original volume. Add heptane (250 mL) to the mixture and stir in an ice-water bath for 30 min. Filter the solid, wash with heptane, and dry at 45° C. in a vacuum oven for 2 days to give the title compound (78.4 g, 68%) as a white solid. ES/MS m/z 326 (M+H).

EXAMPLE 2

4-[(1-Cyclopropyl-2-hydroxy-ethyl)amino]-2-[(4-fluoro-4-methyl-pentyl)amino]pyrimidine-5-carboxamide

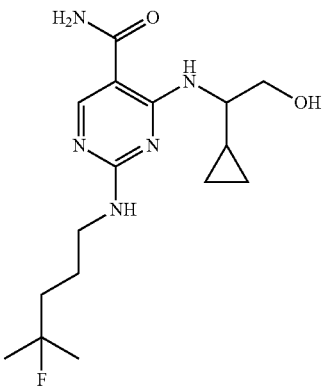 [SMILES: CC(C)(F)CCCNc1ncc(C(N)=O)c(NC(CO)C2CC2)n1]

To a solution of 2,4-dichloropyrimidine-5-carboxamide (300 mg, 1.56 mmol) in NMP (1.5 mL, 16 mmol) at RT add N,N-diisopropylethylamine (0.4 mL, 2 mmol) and then racemic 2-amino-2-cyclopropyl-ethanol (158 mg, 1.56 mmol). Stir the suspension at RT under nitrogen. After 1 h add 4-fluoro-4-methyl-pentan-1-amine acetic acid salt (186 mg, 1.56 mmol), and heat the mixture at 80° C. under nitrogen for 16 h. Cooled the mixture to RT and add water and EtOAc. Separate the organic phase, wash with water and saturated aqueous NaCl. Dry the organics over $Na_2SO_4$, filter, and concentrate. Purify the residue by reverse-phase HPLC using 25-55% acetonitrile/(20 mM aqueous $NH_4HCO_3$) to obtain 163 mg (40%) of the title compound as a white solid. ES/MS m/z 340 (M+H).

EXAMPLE 2A

4-{[(1S)-1-Cyclopropyl-2-hydroxyethyl]amino}-2-[(4-fluoro-4-methylpentyl)amino]pyrimidine-5-carboxamide

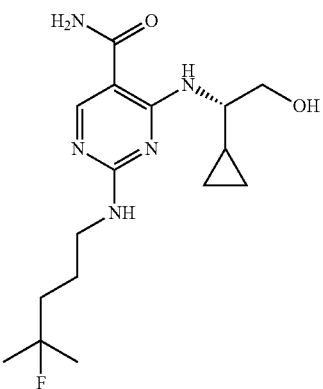 [SMILES: CC(C)(F)CCCNc1ncc(C(N)=O)c(N[C@H](CO)C2CC2)n1]

Purify racemic 4-[(1-cyclopropyl-2-hydroxy-ethyl)amino]-2-[(4-fluoro-4-methyl-pentyl)amino]pyrimidine-5-carboxamide (148 mg, 0.37 mmol) by chiral SFC (column: Chiralpak© IG 25×2 cm, 5 m particle size; column temperature: 40° C.; flow rate: 65 mL/min; eluent: 30% (0.2% dimethylethylamine in isopropanol)/$CO_2$; 10 mg injections every 8 min), the first-eluting isomer giving 52 mg of the title compound as a white solid. ES/MS m/z 340 (M+H).

EXAMPLE 2B

4-{[(1R)-1-Cyclopropyl-2-hydroxyethyl]amino}-2-[(4-fluoro-4-methylpentyl)amino]pyrimidine-5-carboxamide

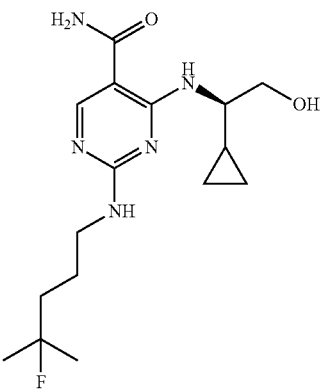 [SMILES: CC(C)(F)CCCNc1ncc(C(N)=O)c(N[C@@H](CO)C2CC2)n1]

Elute the second isomer from the chiral SFC described for Example 2a to give 49 mg of the title compound as a white solid. ES/MS m/z 340 (M+H).

Biological Assays

Biochemical NNMT Inhibition

Biochemical activity of the compounds of the present invention to inhibit human and mouse NNMT enzymes is quantified in a mass spectroscopy-based assay. Test compounds are diluted and acoustically transferred to assay plates, achieving a final DMSO concentration of 2% in the assay. Assay buffer contains 50 mM Tris-HCl at pH of 7.5 (Invitrogen 15567-027) and 0.05 mg/mL fatty acid-free BSA (Sigma A6003). The human NNMT assay is assembled using the Hamilton Nimbus to deliver 10 μM of SAM (S-(5'-adenosyl)-L-methionine) (American Radiolabeled 0768), 15 μM NAM (nicotinamide) (Sigma 72340), and 10 nM full-length, n-terminus his-tagged human NNMT to the assay plate containing diluted test compounds. The corresponding mouse NNMT assay includes 20 μM SAM, 20 μM NAM, and 10 nM mouse NNMT. Max control wells, reflecting full enzyme activity, contain DMSO without test compounds. Min control wells, reflecting no enzyme activity, are identical to the Max control well but without NNMT. After a two-hour incubation at room temperature, 1 part reaction is stopped with 6 parts stop solution containing 158.5 nM $^{13}$C-SAH (S-adenosyl-L-homocysteine (Adenosine-$^{13}C_{10}$)) (Cambridge Isotope Laboratories CLM-8906) and 50 nM $d_7$-methylnicotinamide (BDG Biosynthesis 140138-25) as internal standards. MeNAM (1-methylnicotinamide) and SAH (S-adenosylhomocysteine) levels are measured by RapidFire Mass Spectroscopy and converted to area ratios by dividing the product level by the corresponding internal standard level. The product area ratio is converted to percent inhibition using the following equation: % Inhibition=100−[(Test Compound−Median Min)/(Median Max−Median Min)×100]. The $IC_{50}$ is determined by fitting the percent inhibition at each inhibitor concentration to the following equation using Next Generation Results Rel-$IC_{50}$: Data is analyzed using a 4-paramer nonlinear logistic equation y=(A+((B−A)/(1+((C/x)^D)))) where, y=% specific inhibition, A=bottom of the curve, B=top of the curve, C=relative $IC_{50}$=concentration causing 50% inhibition based on the range of the data from top to bottom D=Hill Slope=slope of the curve.

In this assay, Example 1 inhibits human NNMT with a relative $IC_{50}$ of 74 nM and mouse NNMT with a relative $IC_{50}$ of 21 nM. Example 2a inhibits human NMMT with a relative $IC_{50}$ of 385 nM, and Example 2b inhibits human NNMT with a relative $IC_{50}$ of 57 nM.

In Vivo PD Assay

C57Bl/6 male mice are maintained on a 12 hr light/dark cycle at 22° C. with ad lib access to food (Teklad 2014) and water. Animals are orally dosed with three concentrations (1, 3, and 10 mg/kg) of test compound prior to a subcutaneous injection of 25 mg/kg of deuterated nicotinamide (Cambridge Isotope Laboratories DLM-6883). Plasma is collected at 0, 60, 120, and 240 minutes after injection of deuterated nicotinamide ($d_4$-NAM), and labelled $d_4$-1-methylnicotinamide is quantified via LC/MS according to the method below. The inhibition profiles of test compounds are calculated as an area under the curve (AUC) of the plasma $d_4$-1-MeNAM excursion over the 240-minute assay, and statistically tested via one-way ANOVA (GraphPad Prism 7.03). The resulting AUC calculations show a dose dependent reduction in plasma $d_4$-1-MeNAM in mouse plasma following administration of Example 1 compared to vehicle control (Table 1).

TABLE 1

| Treatment group | $d_4$-1-MeNAM AUC (ng/mL × min) | Standard Error | % AUC Reduction/ Vehicle |
| --- | --- | --- | --- |
| Vehicle | 15449 | ±974 | 0 |
| Example 1 (1 mg/kg) | *5193 | ±257.3 | 66.39% |
| Example 1 (3 mg/kg) | *3315 | ±215.2 | 78.54% |
| Example 1 (10 mg/kg) | *1774 | ±103.8 | 88.52% |

(*P < 0.0001)

LC/MS Method for Quantification of NNMT Reaction Product Deuterated 1-Methylnicotinamide Five microliters of mouse plasma is mixed with forty-five microliters of internal standard solution containing 100 ng/mL of $d_7$-1-MeNAM in water with 0.1% formic acid. Next, two hundred microliters of 1% ammonium hydroxide in acetonitrile is added to each sample, and spun by centrifuge for 10 minutes at 2700×g (4° C.). The upper liquid layer is removed for LC/MS analysis via an isocratic HILIC HPLC method (using a Shimadzu series 30 LC system) composed of 72% acetonitrile and 28% of 20 mM ammonium acetate and 1% ammonium hydroxide in 95% water/ 5% acetonitrile (v/v). The column is a Waters xBridge amide, 3.5 μm, 2.1×50 mm (part #186004859). The mobile phase flow rate is 0.7 mL/min at ambient room temperature. Six microliters of sample are injected for mass spectrometry analysis (Sciex 6500 triplequad) using a 3.6 minute injection cycle. The 1-MeNAM is detected in positive SRM mode using the following transitions: 137.0/94.0 for unlabeled 1-MeNAM, 144.1/101.0 for $d_7$-1-MeNAM, and 141.1/98.1 for $d_4$-1-MeNAM. Analyte peak area determination and quantification is achieved using Sciex MultiQuant version 2.1 software.

What is claimed is:

1. A compound of the formula:

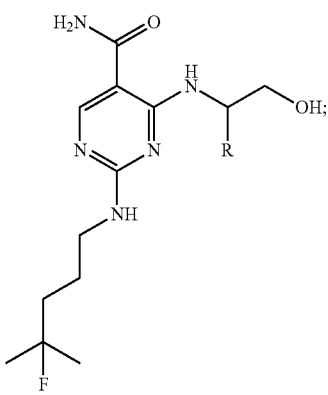

wherein

R is selected from the group consisting of cyclopropyl and geminal cyclopropyl;

or a pharmaceutically acceptable salt thereof.

2. A compound as claimed by claim 1 wherein the compound is

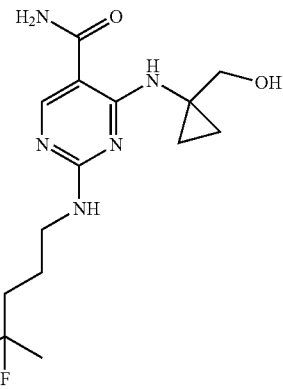

or a pharmaceutically acceptable salt thereof.

3. A compound as claimed by claim 1 wherein the compound is

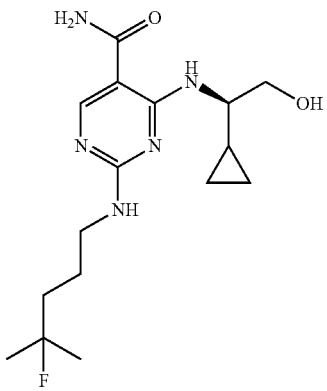 [SMILES: CC(C)(F)CCCNc1ncc(C(N)=O)c(N[C@@H](CO)C2CC2)n1]

or a pharmaceutically acceptable salt thereof.

4. A compound as claimed by claim 1 wherein the compound is

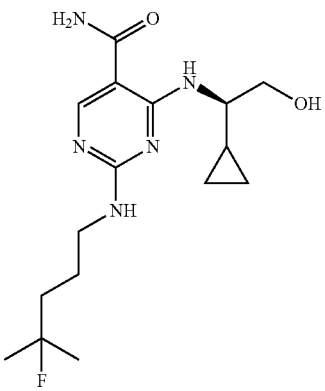 [SMILES: CC(C)(F)CCCNc1ncc(C(N)=O)c(N[C@@H](CO)C2CC2)n1]

or a pharmaceutically acceptable salt thereof.

5. A pharmaceutical composition comprising a compound, or a pharmaceutically acceptable salt thereof, according to claim 1 and at least one pharmaceutically acceptable carrier, diluent, or excipient.

6. A method for treating type 2 diabetes mellitus in a mammal comprising administering to the mammal an effective amount of a compound according to claim 1, or a pharmaceutically acceptable salt thereof.

7. The method according to claim 6 wherein the compound is administered orally.

\* \* \* \* \*

UNITED STATES PATENT AND TRADEMARK OFFICE
CERTIFICATE OF CORRECTION

PATENT NO. : 12,319,658 B2  
APPLICATION NO. : 17/631672  
DATED : June 3, 2025  
INVENTOR(S) : Sra. Gema Ruano Plaza Page 1 of 1

It is certified that error appears in the above-identified patent and that said Letters Patent is hereby corrected as shown below:

In the Claims

In Column 10, Line 23-36:

In Claim 3, delete " 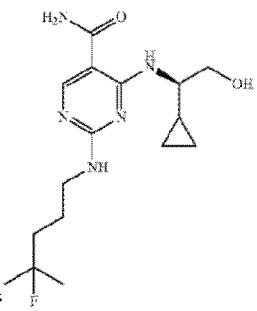 " and insert -- 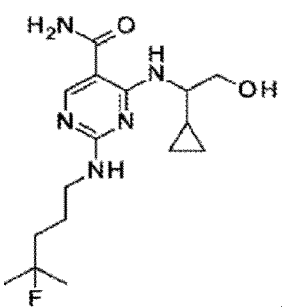 --.

Signed and Sealed this  
Fourteenth Day of October, 2025

John A. Squires  
*Director of the United States Patent and Trademark Office*